(12) United States Patent
Sauermann et al.

(10) Patent No.: US 6,428,779 B1
(45) Date of Patent: Aug. 6, 2002

(54) SKINCARE COMPOSITIONS FOR AGEING SKIN

(75) Inventors: Gerhard Sauermann, Wiemersdorf; Volker Schreiner, Hamburg; Franz Stäb, Echem; Udo Hoppe, Heidmuehlen, all of (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/677,652

(22) Filed: Oct. 3, 2000

Related U.S. Application Data

(62) Division of application No. 09/051,235, filed as application No. PCT/EP96/04302 on Oct. 2, 1996, now Pat. No. 6,261,575.

(30) Foreign Application Priority Data

Oct. 5, 1995 (DE) ........................................ 195 37 027

(51) Int. Cl.[7] .............................. A61K 6/00; A61K 7/00
(52) U.S. Cl. .................................... 424/78.03; 424/401
(58) Field of Search .............................. 424/401, 78.03

(56) References Cited

U.S. PATENT DOCUMENTS 5,693,255 A * 12/1997 Okamoto et al. ........... 252/312

* cited by examiner

Primary Examiner—Thurman K. Page
Assistant Examiner—S. Howard
(74) Attorney, Agent, or Firm—Norris McLaughlin & Marcus

(57) ABSTRACT

Topical formulations containing one or more compounds chosen from the group (A) consisting of sterols and biochemical precursors thereof in combination with a content of one or more compounds chosen from the group (B) consisting of ubiquinones and derivatives thereof and plastoquinones and derivatives thereof.

15 Claims, No Drawings

SKINCARE COMPOSITIONS FOR AGEING SKIN

This application is a division of U.S. Ser. No. 09/051,235, filed on Aug. 14, 1998, now U.S. Pat. No. 6,261,575, which is a 371 of PCT/EP96/04302, filed on Oct. 2, 1996. Benefit thereof is claimed.

Skin ages as a result of endogenous, genetically determined influences. Exogenous factors, such as UV light and chemical noxae, can have a cumulative effect and accelerate the natural ageing processes. This results in numerous degenerative processes which lead, depending on the extent of the influencing factors, inter alia, to the following structural changes and damage in the dermis and epidermis (e.g. also to dermatoheliosis):

a) Degeneration of the microvascular system.
b) Flaccidity and development of wrinkles, partly due to a decrease in and crosslinking of collagen, accumulation of glucosaminoglycans (base substance) and solar elastosis (elastin clumping).
c) Flattening of the retial cones. This is associated with the reduction in the area between the dermis and epidermis via which substances are exchanged for nutrition and purification of the epidermis.
d) Restricted regenerative turnover in the epidermis, associated with defective development of the horny layer (disturbed hornification), leading to drying out of the skin, to roughness of the skin and to chapping of the skin.
e) Defective regulation of cell division (proliferation) and cell maturation (differentiation) in the epidermis, which results in cellular atypia and atrophies and the loss in polarity.
f) Local hyper- and hypopigmentation and abnormal pigmentation (age spots).

The present invention relates to products for the care and prophylaxis of ageing skin, in particular skin which has been aged by light and skin which has been chronologically aged by endogenous mechanisms, and also to the treatment of damage caused by light-ageing and ageing of the skin caused endogenously, in particular of the phenomena listed under a) to f), and, preferably, to the treatment and prophylactic treatment of wrinkles and roughness of the skin.

Products for the care, prophylaxis and treatment of skin which has been aged by light are known per se. They comprise, for example, retinoids (vitamin A acid and/or derivatives thereof) or vitamin A and/or derivatives thereof. However, the extent of their action on the structural damage in cases of light-ageing is limited. The use of products containing vitamin A acid furthermore often causes severe erythematous skin irritations.

Also known, from DE-A-33 09 850, are cosmetic formulations containing coenzyme Q-10, which are suitable for the treatment of skin diseases, for the prophylaxis of dystrophic and dysmetabolic states of the skin and for use on chemical and physical respiratory damage or in cases of delayed respiration associated with age and wear.

JP-A-58,180,410 describes the suitability of coenzyme Q-10 for cosmetics. It is said to activate skin cell metabolism and to suppress oxidation. As a result, coenzyme Q-10 has an important function in the prevention of skin damage caused by UV rays and the prevention of skin ageing. The roughness of the skin of 20- to 40-year olds is improved by giving the skin moisture.

The object of the present invention was thus to find ways of avoiding the disadvantages of the prior art. In particular, the prophylactic effect and the restructuring action in cases of skin ageing was to be permanent, sustained and without the risk of side effects.

According to the invention, these objects are achieved by skincare preparations and active substance combinations which contain sterols and biochemical precursors thereof in combination with ubiquinones and/or plastoquinones.

The invention relates to topical formulations containing one or more compounds chosen from the group (A) consisting of sterols and biochemical precursors thereof in combination with a content of one or more compounds chosen from the group (B) consisting of ubiquinones and derivatives thereof and plastoquinones and derivatives thereof.

Examples of highly suitable sterols are zoosterols, phytosterols and mycosterols.

Preferred zoosterols are cholesterol, dihydrocholesterol, 7-dehydrocholesterol, lanosterol, dihydrolanosterol, spongosterol and stellasterol.

Preferred phytosterols are ergosterol, sitosterol, stigmasterol, fucosterol, brassicasterol and campesterol.

Preferred mycosterols are ergosterol, fungisterol and zymosterol.

Preferred biochemical precursors of sterols are mevalonic acid, farnesol and squalane.

Particularly preferred compounds of the group (A) are cholesterol, 7-dehydrocholesterol, dihydrocholesterol, lanosterol, dihydrolanosterol, spongosterol and stellasterol.

Preferred formulations contain one, two or three compounds chosen from the group (A) combined with one, two or three compounds from the group (B).

The topical formulations according to the invention can be cosmetic or dermatological formulations. They are used, as are also the active substances, for the care and prophylaxis in cases of light-ageing and chronological skin ageing and for the treatment of light-aged skin and chronologically aged skin.

The invention also relates to the use of topical formulations containing one or more compounds chosen from the group (A) consisting of sterols and biochemical precursors thereof in combination with a content of one or more compounds chosen from the group (B) consisting of ubiquinones and derivatives thereof and plastoquinones and derivatives thereof for the care and prophylaxis in cases of light-ageing and chronological skin ageing and for the treatment of light-aged skin and chronologically aged skin.

The active substance combinations according to the invention and the formulations obtainable therewith effect restructuring of light-aged skin or skin aged chronologically by endogenous mechanisms, in particular of wrinkled, rough, dry, chapped and/or flaky skin.

The invention thus also relates to the use of the above formulations and active substances for the purposes described, but preferably to the use for the prophylaxis and treatment of the following symptoms a) to f), in particular of dermatoheliosis and of chronologically aged skin:

a) Degeneration of the microvascular system.
b) Flaccidity and development of wrinkles, partly due to a decrease in and crosslinking of collagen, accumulation of glucosaminoglycans (base substance) and solar elastosis (elastin clumping).
c) Flattening of the retial cones. This is associated with the reduction in the area between the dermis and epidermis via which substances are exchanged for nutrition and purification of the epidermis.
d) Restricted regenerative turnover in the epidermis, associated with defective development of the horny layer (disturbed hornification), leading to drying out of the skin, to roughness of the skin, chapping of the skin and flaking.

e) Defective regulation of cell division (proliferation) and cell maturation (differentiation) in the epidermis, which results in cellular atypia and atrophies and the loss in polarity.

f) Local hyper- and hypopigmentation and abnormal pigmentation (age spots).

Particular preference is given to combinations of cholesterol with ubiquinones, in particular coenzyme Q-6, Q-9 or Q-10, but in particular to combinations of cholesterol with coenzyme Q-10, to formulations therewith, and to the uses for the above purposes.

Ubiquinones (also coenzymes $Q_n$) are a group of substances which have n isoprene units bonded in the form of a chain on their quinone ring ($Q_0$–$Q_{10}$). Ubiquinones function as electron transfer agents in biological, mitochondrial oxidation and thus play an important role in energy metabolism of the cells. Plastoquinones are analogous compounds from the plant kingdom, which play a role in photosynthesis. Ubiquinones have been used for a long time in cosmetic formulations as antioxidants for protection of oxidation-sensitive substances against decay induced by oxygen free radicals.

"Ubiquinones" and "plastoquinones" here also mean "ubiquinones and derivatives thereof" and "plastoquinones and derivatives thereof".

Ubiquinones are known from the literature (for example "Römpp Chemie Lexikon" [Römpp's Chemical Dictionary], Georg Thieme Verlag Stuttgart, New York, 9th Edition, pages 4784–4785 or "The Merck Index", 11th Edition, Merck & Co., Inc. Rahway, N.Y., USA, Abstr. 9751 (1989)). They are also called mitoquinones or coenzymes Q. The number of isoprene units in the side chain is indicated by n in the term coenzymes Q–n, wherein n is an integer. Preference is given to ubiquinones or coenzymes Q–n where n=0–12, particularly preferably n=1–12, and in particular n=6 to 10. The invention thus also relates to the quinone parent substance of ubiquinone without isoprene substituents. Other examples of novel ubiquinones or derivatives thereof are alkylubiquinones, in particular 6-alkylubiquinones with preferably $C_1$–$C_{12}$-alkyl radicals. Preference is given to decylubiquinone, in particular 6-decylubiquinone, or 2,3-dimethoxy-5-methyl-6-decyl-1,4-benzoquinone.

The plastoquinones are likewise known from the literature (for example "Römpp Chemie Lexikon" [Römpp's Chemical Dictionary], Georg Thieme Verlag, Stuttgart, New York, 9th Edition, page 3477). They are closely related to the ubiquinones in structure and are also counted among the isoprenoid quinones, since they carry a side chain of isoprene units on the quinone ring. Preferred plastoquinones are those having 0–12, particularly preferably 1–10, and in particular from 6 to 10, isoprene units in the side chain. The invention thus also relates to the quinone parent substance of plastoquinone without isoprene substituents.

Further examples of plastoquinones according to the invention or derivatives thereof are alkylplastoquinones with preferably $C_1$–$C_{12}$-alkyl radicals. Preference is given to decylplastoquinones, in particular 5- or 6-decylplastoquinone, or 2,3-dimethyl-5-decyl-1,4-benzoquinone.

Ubiquinones function as electron transfer agents in biological, mitochondrial oxidation and thus play an important role in the energy metabolism of animal cells. Ubiquinones have been used for a long time in cosmetic formulations as antioxidants for protection of oxidation-sensitive substances.

Plastoquinones are analogous compounds from the plant kingdom, which play a role in photosynthesis in the chloroplasts of plant cells. They differ from ubiquinones in three substituents on the quinone ring, where the two methoxy groups in the ubiquinones are replaced by methyl groups and one methyl group is replaced by a hydrogen atom. However, the isoprene units bonded in the form of a chain have the same structure (cf., for example, Pfister and Arntzen, Z. für Naturforschung C34; 996 et seq., 1979).

Particular preference is given to the following active substances according to the invention and combinations therewith:

coenzyme Q-10, coenzyme Q-9, coenzyme Q-8, coenzyme Q-7, coenzyme Q-6, and plastoquinone with 10 isoprene units (also called PQ-10, in accordance with the IUB abbreviation PQ for plastoquinones, in the formula PQ–n, n is intended to indicate the number of isoprene units (0 to 12)), PQ-9, PQ-8, PQ-7, PQ-6.

Surprisingly, it has been found that sterols or biochemical precursors thereof, in combination with ubiquinones and/or plastoquinones, interact in a synergistic manner in the protection against light-ageing and chronological skin ageing and in the repair of structural damage to the skin caused by light and caused endogenously, which significantly remedies the disadvantage of the prior art.

The concentrations of sterols and biochemical precursors thereof in topical formulations are preferably between 0.01 and 99% by weight.

The concentrations of ubiquinones and/or plastoquinones in topical formulations are preferably between 0.001 and 99% by weight.

Formulations, skincare products or dermatological preparations according to the invention advantageously comprise the following combinations:

0.01–10% by weight of sterols and biochemical precursors thereof and 0.001–10% by weight of ubiquinone and/or plastoquinone Topical formulations or dermatological preparations preferably comprise 0.05–1% by weight of cholesterol 0.05–1% by weight of coenzyme $Q_{10}$ The formulations or dermatological preparations very particularly preferably comprise 0.4% by weight of cholesterol 0.4% by weight of coenzyme $Q_{10}$ In the context of the application, percentages by weight are always based on 100% by weight of the total composition of the particular skincare preparations or dermatological formulation according to the invention.

The active substance combinations or active substances according to the invention can be present in the topical formulations in amounts of from 0.001 to 99% by weight, for example also in amounts of from 0.001 to 50% by weight, in each case based on the total weight of the formulations.

The active substance combinations or active substances according to the invention can preferably be present in the topical formulations in amounts of from 0.01 to 10% by weight, in particular in amounts of from 0.1 to 1% by weight, in each case based on the total weight of the formulations.

The weight ratios of the two components in the combinations can vary within wide ranges, for example in the ratio from 1:100 to 100:1, preferably in the ratio from 1:10 to 10:1. The components can also be present, for example, in the weight ratio from 1:2 to 2:1 or 1:1.

Topical formulations or compositions according to the invention containing the combinations and active substances according to the invention are all the customary use forms, for example creams (W/O, O/W or W/O/W), gels, lotions or milks.

The topical formulations according to the invention can be formulated as liquid, pasty or solid formulations, for example as aqueous or alcoholic solutions, aqueous suspensions, emulsions, ointments, creams, oils, powders or sticks. Depending on the desired formulation, the active substances can be incorporated into pharmaceutical and cosmetic bases for topical applications, which comprise, as further components, for example, oil components, fats and waxes, emulsifiers, anionic, cationic, ampholytic, zwitterionic and/or nonionic surfactants, lower mono- and polyhydric alcohols, water, preservatives, buffer substances, thickeners, fragrances, dyestuffs and opacifying agents. The active substances according to the invention can also advantageously be used in transdermal therapeutic systems, in particular cubic systems.

It is furthermore advantageous to add to the formulations antioxidants (for example alpha-tocopherol, vitamin E and C, flavones, flavonoids, imidazoles, alpha-hydroxycarboxylic acids (for example malic acid, glycolic acid, gluconic acid, salicylic acid and derivatives thereof) and/or iron-complexing agents (for example EDTA and alpha-hydroxy-fatty acids) and/or known UV light protection filters, in amounts of, for example, from 0.1 to 10 per cent by weight, in order to ensure the stability of the oxidation-sensitive active substances.

It is also advantageous to add to the formulations, in particular, from 0.01–10 per cent by weight of substances or substance combinations of aerobic cellular energy metabolism, for example cellular energy transfer agents (such as creatine, guanine, guanosine, adenine, adenosine, nicotine, nicotinamide or riboflavin), coenzymes (for example pantothenic acid, panthenol, lipoic acid or niacin), auxiliary factors (for example L-carnitine, dolichol or uridine), substrates (for example hexoses, pentoses or fatty acids) and intermediate metabolism products (for example citric acid or pyruvate) and/or glutathione.

It is also advantageous to add to the formulations penetration promotors, in particular oleic acid, cis-6-hexadecenoic acid or palmitoleic acid. Penetration promotors can be present in the formulations in amounts of from 0.01% by weight to 1.0% by weight.

It is also advantageous to add ceramides to the formulations. They may be present in the formulations in amounts of from 0.01% by weight to 5.0% by weight.

Formulations according to the invention can furthermore advantageously comprise substances which absorb UV radiation in the UVA and/or in the UVB region, the total amount of filter substances being, for example, from 0.1% by weight to 30% by weight, preferably from 0.5 to 10% by weight, in particular from 1.0 to 6.0% by weight, based on the total weight of the formulations, to provide cosmetic formulations which protect the skin from the entire region of ultraviolet radiation. They can also be used as sunscreens for the skin. In the formulations, the UV absorbers act as antioxidants with respect to the active substances.

If the emulsions according to the invention comprise UVB filter substances, these can be oil-soluble or water-soluble. Examples of oil-soluble UVB filters which are advantageous according to the invention are: 3-benzylidenecamphor derivatives, preferably 3-(4-methyl-benzylidene)camphor and 3-benzylidenecamphor.

Examples of advantageous water-soluble UVB filters are: salts of 2-phenylbenzimidazole-5-sulphonic acid, such as its sodium, potassium or its triethanolammonium salt, and the sulphonic acid itself.

It may also be advantageous to combine active substance combinations according to the invention with UVA filters which have hitherto usually been present in cosmetic formulations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. These combinations and formulations which comprise these combinations are also provided by the invention. The amounts used for the UVB combination can be employed.

The invention thus also relates to the combinations of the active substances according to the invention, in particular in the topical formulations, with antioxidants, substances of aerobic cellular energy metabolism and/or UV absorbers, with which, for example, the stability and the action of the formulation can be improved.

The abovementioned examples of active substances which can be combined from the stated groups of active substances serve to describe the invention, without the intention being to limit the invention to these examples.

It is moreover possible to use protective formulation forms, the substances according to the invention being enclosed (encapsulated), for example, in liposomes, micelles, nanospheres, etc. of, for example, hydrogenated amphiphiles, such as, for example, ceramides, fatty acids, sphingomyelin and phospho-glycerides, or in cyclodextrans. Further protection can be achieved by the use of protective gas (for example $N_2$, $CO_2$) during formulation and the use of gas-tight packaging.

Further auxiliaries and additives may be water-binding substances, thickeners, fillers, perfume, dyes, emulsifiers, active substances such as vitamins, preservatives, water and/or salts.

During processing of the active substances and other oxidation-sensitive substances, the temperature should not exceed 40° C. The customary rules, which are known to the person skilled in the art, are otherwise to be observed.

The substance groups according to the invention can thus be incorporated into all cosmetic bases. In principle, however, W/O, O/W and W/O/W emulsions are preferred. Combinations according to the invention can be particularly advantageously employed in care products such as, for example, O/W creams, W/O creams, O/W lotions, W/O lotions, etc.

The invention also relates to the combinations of the active substances according to the invention.

Unless stated otherwise, all the quantity data, percentage data or parts are based on the weight, in particular on the total weight of the formulations or of the particular mixture.

The following examples serve to describe the invention, without the intention being to limit the invention to these examples.

| Combination | A | B | C | D | E | F |
|---|---|---|---|---|---|---|
| Cholesterol | 50 | 50 | 10 | 90 | 60 | 50 |
| Coenzyme $Q_9$ | — | 25 | — | — | — | 40 |
| Coenzyme $Q_{10}$ | 50 | 25 | 90 | 10 | 40 | 10 |
| | 100 | 100 | 100 | 100 | 100 | 100 |

The parts and numerical data are based on parts by weight.

EXAMPLE I

With Combination A

W/O skin cream

| | Parts by weight |
|---|---|
| Vaseline DAB 9 | 13 |
| Glycerol DAB 9 | 6.3 |
| Water, deionized | 34.4 |
| Paraffin oil (Hineral oil 5E, Shell) | 31 |
| Cetearyl alcohol/PEG 40 castor oil/sodium cetearyl sulphate (Emulgade F, Henkel KGaA) | 2.5 |

0.3 part of coenzyme $Q_{10}$, dissolved in 3 parts of paraffin oil, is incorporated into the fat phase, which has been heated to 75° C. The fat phase is then added to the aqueous phase, which has been heated to 75° C., and the mixture is stirred and homogenized until a homogeneous pale yellow cream has formed. 0.3 part of cholesterol is dissolved in a further 3.2 parts of paraffin oil at room temperature and the solution is stirred into the cooled cream.

Example I has the following final composition:

| | Parts by weight |
|---|---|
| Vaseline DAB 9 | 13 |
| Glycerol DAB 9 | 6.3 |
| Water, deionised | 34.4 |
| Paraffin oil (Mineral oil 5E, Shell) | 43.2 |
| Cetearyl alcohol/PEG 40 castor oil/sodium cetearyl sulphate (Emulgade F, Henkel KGaA) | 2.5 |
| Cholesterol | 0.3 |
| Coenzyme $Q_{10}$ | 0.3 |
| | 100 |

EXAMPLE II

With Combination B

W/O skin cream

| | Parts by weight |
|---|---|
| PEG 1-glyceryl oleostearate + paraffin wax | 8 |
| Vaseline DAB | 2.8 |
| Paraffin wax/paraffin | 1.8 |
| Ceresin | 2.2 |
| Octyldodecanol (Eutanol G, Henkel KGaA) | 10 |
| Propylene glycol | 1 |
| Glycerol | 1 |
| Magnesium sulphate | 0.7 |
| Water, deionized | 59.7 |
| Total additives (perfume, preservation, stabilization) | 0.8 |

0.2 part of coenzyme $Q_{10}$ and 0.2 part of coenzyme $Q_9$, dissolved in 6 parts of paraffin oil, are incorporated into the fat phase, which has been heated to 75° C. The fat phase is then added to the aqueous phase, which has been heated to 75° C., and the mixture is stirred and homogenized until a homogeneous pale yellow cream has formed. 0.4 part of cholesterol are dissolved in a further 5.5 parts of paraffin oil, at room temperature, and the solution is stirred into the cooled cream.

Example II has the following final composition:

| | Parts by weight |
|---|---|
| PEG 1-glyceryl oleostearate + paraffin wax | 8 |
| Vaseline DAB | 2.8 |
| Paraffin wax/paraffin | 1.8 |
| Paraffin oil (Mineral oil 5E, Shell) | 11.5 |
| Ceresin | 2.2 |
| Octyldodecanol | 10 |
| Cholesterol | 0.4 |
| Coenzyme $Q_9$ | 0.2 |
| Coenzyme $Q_{10}$ | 0.2 |
| Propylene glycol | 1 |
| Glycerol | 1 |
| Magnesium sulphate | 0.7 |
| Water, deionized | 59.4 |
| Total additives (perfume, preservative, stabilization) | 0.8 |
| | 100 |

EXAMPLE III

With Combination C

O/W skin cream

| | Parts by weight |
|---|---|
| Octyldodecanol (Eutanol G, Henkel KGaA) | 9.3 |
| Cetearyl alcohol/PEG 40 castor oil/sodium cetearyl sulphate (Emulgade F, Henkel KGaA) | 3.7 |
| Water, deionized | 73.7 |
| Glycerol DAB 9 | 4.6 |

0.9 part of coenzyme $Q_{10}$, dissolved in 4 parts of paraffin oil, is incorporated into the fat phase, which has been heated to 75° C. The fat phase is then added to the aqueous phase, which has been heated to 75° C., and the mixture is stirred and homogenized until a homogeneous pale yellow cream has formed. 0.1 part of cholesterol is dissolved in a further 3.7 parts of paraffin oil at room temperature and the solution is stirred into the cooled cream.

Example III has the following final composition:

| | Parts by weight |
|---|---|
| Octyldodecanol (Eutanol G, Henkel KGaA) | 9.3 |
| Cetearyl alcohol/PEG 40 castor oil/sodium cetearyl sulphate (Emulgade F, Henkel KGaA) | 3.7 |
| Water, deionized | 73.7 |
| Glycerol DAB 9 | 4.6 |
| Paraffin oil (Mineral oil 5E, Shell) | 7.7 |

-continued

|  | Parts by weight |
|---|---|
| Coenzyme $Q_{10}$ | 0.9 |
| Cholesterol | 0.1 |
|  | 100 |

EXAMPLE IV

With Combination D

| O/W lotion | |
|---|---|
|  | Parts by weight |
| Steareth-2 | 3 |
| Steareth-21 | 2 |
| Cetearyl alcohol/PEG 40 castor oil/sodium cetearyl sulphate (Emulgade F, Henkel KGaA) | 2.5 |
| Propylene glycol | 1 |
| Glycerol | 1 |
| Water, deionized | 74.3 |
| Total additives (perfume, preservative, stabilization) | 0.8 |

0.1 part of coenzyme $Q_{10}$, dissolved in 5.2 parts of paraffin oil, is incorporated into the fat phase, which has been heated to 75° C. The fat phase is then added to the aqueous phase, which has been heated to 75° C., and the mixture is stirred and homogenized until a homogeneous pale yellow lotion has formed. 0.9 part of cholesterol is dissolved in a further 9 parts of paraffin oil at room temperature and the solution is stirred into the cooled lotion.

Example IV has the following final composition:

|  | Parts by weight |
|---|---|
| Steareth-2 | 3 |
| Steareth-21 | 2 |
| Cetearyl alcohol/PEG 40 castor oil/sodium cetearyl sulphate (Emulgade F, Henkel KGaA) | 2.5 |
| Paraffin oil (Mineral oil 5E, Shell) | 14.4 |
| Propylene glycol | 1 |
| Coenzyme $Q_{10}$ | 0.1 |
| Cholesterol | 0.9 |
| Glycerol | 1 |
| Water, deionized | 74.3 |
| Total additives (perfume, preservative, stabilization) | 0.8 |
|  | 100 |

EXAMPLE V

With Combination E

| O/W lotion | |
|---|---|
|  | Parts by weight |
| Octyldodecanol (Eutanol G, Henkel KGaA) | 5.6 |
| Cetearyl alcohol/PEG 40 castor oil/sodium cetearyl sulphate (Emulgade F, Henkel KGaA) | 8.9 |
| Cetearyl isononanoate (Cetiol SN, Henkel KGaA) | 7.5 |
| Water, deionized | 62.3 |
| Glycerol DAB 9 | 4.7 |

0.4 part of coenzyme $Q_{10}$, dissolved in 6 parts of paraffin oil, is incorporated into the fat phase, which has been heated to 75° C. The fat phase is then added to the aqueous phase, which has been heated to 75° C., and the mixture is stirred and homogenized until a homogeneous pale yellow lotion has formed. 0.6 part of cholesterol are dissolved in a further 4 parts of paraffin oil at room temperature and the solution is stirred into the cooled lotion.

Example V has the following final composition:

|  | Parts by weight |
|---|---|
| Octyldodecanol (Eutanol G, Henkel KGaA) | 5.6 |
| Cetearyl alcohol/TEG 40 castor oil/sodium cetearyl sulphate (Emulgade F, Henkel KGaA) | 8.9 |
| Cetearyl isononanoate (Cetiol 5N, Henkel KGaA) | 7.5 |
| Water, deionized | 62.3 |
| Glycerol DAB 9 | 4.7 |
| Paraf fin oil (mineral oil 5E, Shell) | 10 |
| Coenzyme $Q_{10}$ | 0.4 |
| Cholesterol | 0.6 |
|  | 100 |

EXAMPLE VI

With Combination F

| Skin oil | |
|---|---|
|  | Parts by weight |
| Glyceryl tricaprylate (Miglyol 812, Dynamit Nobel) | 21 |
| Hexyl laurate (Cetiol A, Henkel KGaA) | 20 |
| Octyl stearate (Cetiol 886, Henkel KGaA) | 20 |
| Paraffin oil (Mineral oil 5E, Shell) | 35 |
| Cholesterol | 2 |
| Coenzyme $Q_9$ | 1.6 |
| Coenzyme $Q_{10}$ | 0.4 |
|  | 100 |

The components are stirred at 25° C. until a homogeneous, clear mixture has formed.

What is claimed is:

1. A cosmetic or dermatological composition intended to be topically applied to skin, said composition comprising a combination of:
   (A) one or more compounds selected from the group consisting of sterols; and
   (B) on or more compounds selected from the group consisting of ubiquinones, derivatives of ubiquinones, plastoquinones and derivatives of plastoquinones.

2. The composition according to claim 1, which comprises one, two or three compounds from (A) combined with one, two or three compounds from (B).

3. The composition according to claim 1, which comprises one or more zoosterols.

4. The composition according to claim 3, which comprises cholesterol.

5. The composition according to claim 1, which comprises one or more ubiquinones.

6. The composition according to claim 5, wherein the ubiquinones have 0 to 12 isoprene units and optionally one or more alkyl radicals.

7. The composition according to claim 6, wherein the ubiquinones have 9 or 10 isoprene units.

8. The composition according to claim 1, which comprises one or more plastoquinones.

9. The composition according to claim 8, wherein the plastoquinones have 0 to 12 isoprene units.

10. The composition according to claim 9, wherein the plastoquinones have 9 or 10 isoprene units.

11. The composition according to claim 1, which further comprises at least one member selected from the group consisting of antioxidants, substances of aerobic cellular energy metabolism and UV absorbers.

12. The composition according to claim 1, which is in the form of a water-in-oil (W/O) emulsion.

13. The composition according to claim 1, which is in the form of an oil-in-water (O/W) emulsion.

14. The composition according to claim 1, which is in the form of a water-in-oil-in-water (W/O/W) emulsion.

15. The composition according to claim 1, which comprises a combination of:
   (A) cholesterol; and
   (B) co-emzyme $Q_{10}$.

* * * * *